US007997508B2

(12) United States Patent
Motylinski et al.

(10) Patent No.: US 7,997,508 B2
(45) Date of Patent: Aug. 16, 2011

(54) SPILL-PROOF AERATOR FOR LOW VOLATILE COMPOUND SOLUTIONS

(75) Inventors: Nathan Motylinski, Raleigh, NC (US); Ali Alexandre Mehfar, Raleigh, NC (US)

(73) Assignee: Le Cherche Midi, Raleigh, NC (US)

( * ) Notice: Subject to any disclaimer, the term of this patent is extended or adjusted under 35 U.S.C. 154(b) by 114 days.

(21) Appl. No.: 12/426,660

(22) Filed: Apr. 20, 2009

(65) Prior Publication Data

US 2010/0038442 A1 Feb. 18, 2010

Related U.S. Application Data

(60) Provisional application No. 61/089,088, filed on Aug. 15, 2008.

(51) Int. Cl.
*A61L 9/04* (2006.01)

(52) U.S. Cl. ................ 239/6; 239/34; 239/44; 239/145; 239/600; 215/355

(58) Field of Classification Search ................ 239/6, 34, 239/44, 45, 47, 145, 326, 600; 220/694; 215/355, 356, 386
See application file for complete search history.

(56) References Cited

U.S. PATENT DOCUMENTS

| | | | | |
|---|---|---|---|---|
| 1,123,036 | A | 12/1914 | Tiemann | |
| 1,129,897 | A | 3/1915 | Owen, Jr. | |
| 2,283,028 | A | 5/1942 | Bailey | |
| 3,587,968 | A | 6/1971 | Hennart et al. | |
| 4,286,754 | A | 9/1981 | Jones | |
| 4,413,779 | A | 11/1983 | Santini | |
| 4,419,326 | A | 12/1983 | Santini | |
| 4,739,928 | A * | 4/1988 | O'Neil | 239/45 |
| 4,915,301 | A | 4/1990 | Munteanu | |
| D318,912 | S | 8/1991 | von Philipp et al. | |
| 5,047,234 | A * | 9/1991 | Dickerson et al. | 239/44 |
| 5,242,111 | A | 9/1993 | Nakoneczny et al. | |
| D380,538 | S | 7/1997 | Muller et al. | |
| RE38,150 | E * | 6/2003 | Greatbatch et al. | 239/44 |
| 6,708,897 | B1 * | 3/2004 | Hart et al. | 239/45 |
| 7,000,852 | B1 | 2/2006 | Chiu | |
| 7,140,553 | B2 * | 11/2006 | Zobele | 239/34 |

(Continued)

FOREIGN PATENT DOCUMENTS

| | | | |
|---|---|---|---|
| EP | 1 834 653 | A2 | 9/2007 |
| EP | 2 047 868 | A2 | 4/2009 |
| EP | 2 070 554 | A1 | 6/2009 |
| FR | 2857137 | A1 | 3/2006 |
| JP | 404327854 | A | 11/1992 |
| WO | WO 98/16262 | | 4/1998 |

OTHER PUBLICATIONS

PCT International Search Report, International Application No. PCT/US2009/053284, Internationall Filing Date: Aug. 10, 2009, 4 pages.

*Primary Examiner* — Steven J Ganey
(74) *Attorney, Agent, or Firm* — Fay Sharpe LLP

(57) ABSTRACT

A spill-proof aerator is disclosed that is adapted to flamelessly diffuse a liquid solution into the atmosphere. The device comprises a liquid solution having less than 20% volatile organic compounds housed in a vessel with at least one wall, wherein an opening is disposed in the wall. The device further includes a wick assembly including at least a wick of porous material capable of being disposed in the opening of the vessel for at least partial submergence in the liquid solution. The wick is further disposed for drawing up the liquid solution thorough capillary action. The wick assembly is reusable and adapted to removably seal the opening in the vessel.

22 Claims, 10 Drawing Sheets

U.S. PATENT DOCUMENTS

| | | |
|---|---|---|
| 7,252,244 B2 | 8/2007 | Martins, III |
| 7,309,024 B2 * | 12/2007 | Hansen et al. .................... 239/6 |
| 7,469,842 B2 | 12/2008 | Martins, III |
| 2005/0199742 A1 | 9/2005 | Maat |
| 2006/0289669 A1 * | 12/2006 | McGee et al. ................. 239/45 |
| 2007/0122306 A1 | 5/2007 | Brown et al. |
| 2007/0125874 A1 | 6/2007 | Alexander |
| 2008/0093475 A1 | 4/2008 | Belongia et al. |
| 2008/0267832 A1 | 10/2008 | Chen |

* cited by examiner

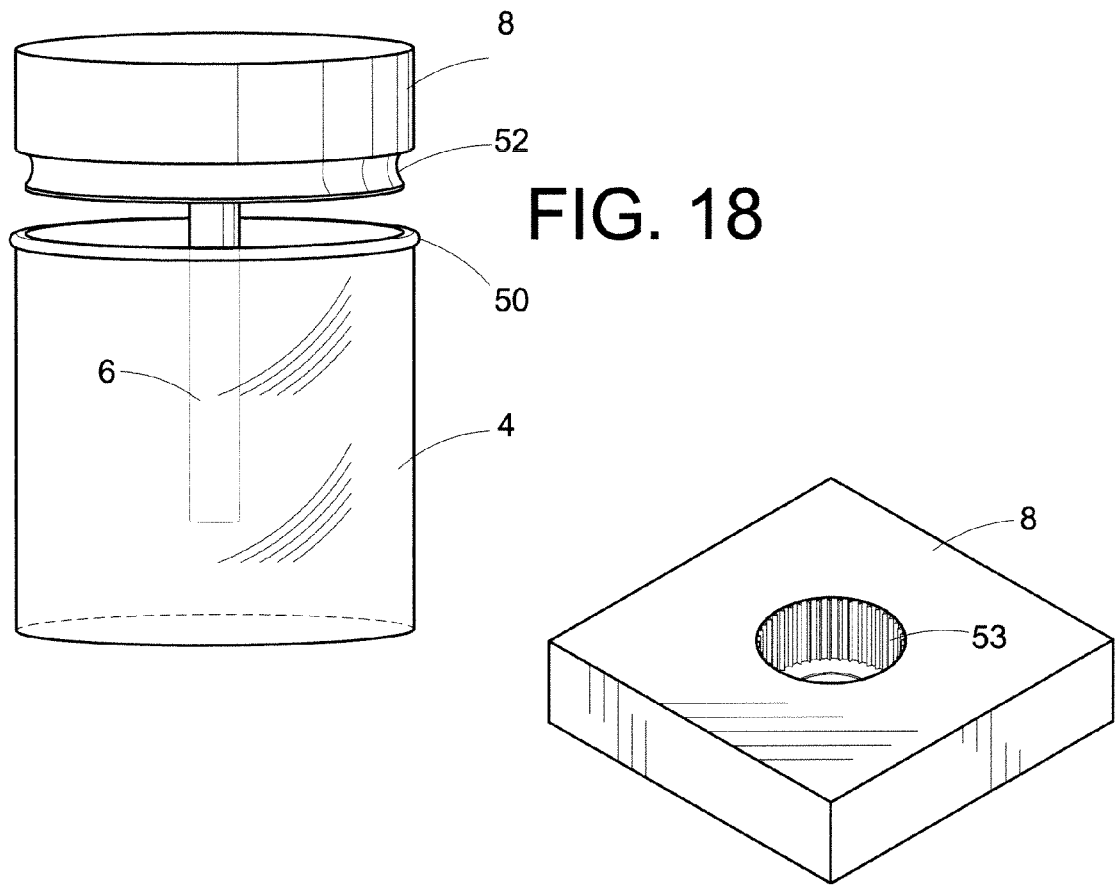
FIG. 18
FIG. 19
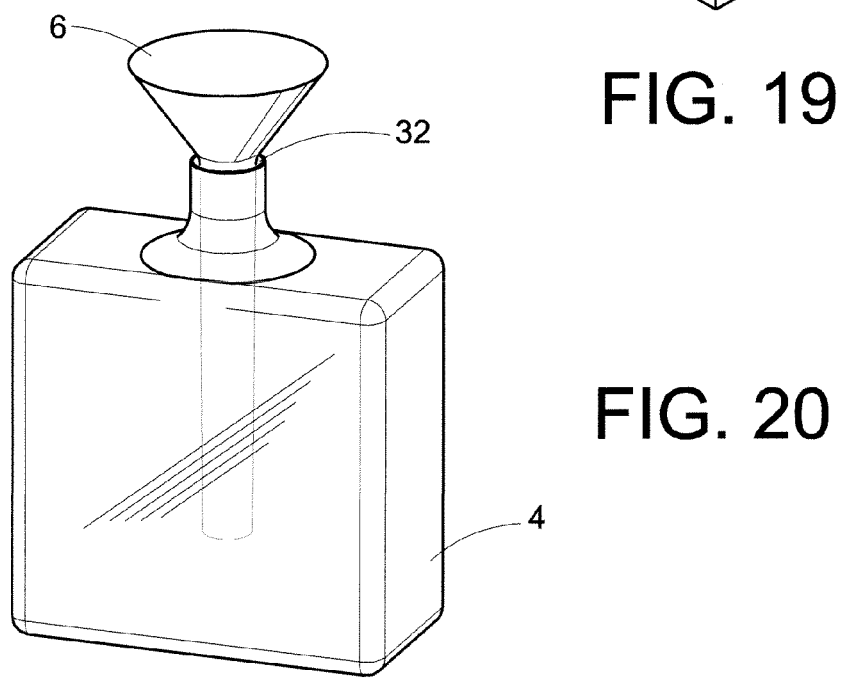
FIG. 20

SPILL-PROOF AERATOR FOR LOW VOLATILE COMPOUND SOLUTIONS

This application claims the priority benefit of U.S. Provisional Application No. 61/089,088, filed Aug. 15, 2008, the disclosure of which is incorporated herein in its entirety by reference.

BACKGROUND

The present exemplary embodiment relates to an apparatus for dispersing low volatile organic compound (VOC) liquid solutions into the atmosphere. It finds particular application in conjunction with flameless, environmental fragrance diffusers, and will be described with particular reference thereto. However, it is to be appreciated that the present exemplary embodiment is also amenable to other like applications.

Over the past decade, fragrance diffusers have increased in popularity as consumers look for safe, non-flammable ways to scent their environments. Particularly, reed diffusers have quickly become household staples as a safe way to fill a space with fragrance while avoiding the dangers of candles. Additionally, the reed diffusers provide long-lasting scent while being both economical and attractive. Fragrance reed diffusers are all generally similar in form and consist of a glass container, a set of reeds and diffuser solution, as illustrated in FIG. 1. The glass bottle is filled about three quarters of the way full of the diffuser solution and the reeds are inserted into the solution. The reeds "wick," or draw up the diffuser solution through channels disposed in each reed. The scent is then dispersed into the air through evaporation and the natural properties of the generally high volatile organic compounds in the fragrance solution "lift" the fragrance into the air.

Reed diffusers possess numerous disadvantages that cause such diffusers to be less desirable to a consumer. For instance, reed diffusers are not maintenance free, but rather require users to flip or turn the reeds about once a week to refresh the scent. Another known disadvantage is that diffusers are not spill-proof. The required reed flipping may cause the diffuser solution to spill onto the user's hands or surface top on which the diffuser rests. The diffusers generally have open tops into which the reeds or sticks are inserted. The reeds do not seal-off the opening and thereby leave the solution exposed to the air and vulnerable to spilling out of the diffuser. Therefore, current diffusers are not suitable for all environments, such as vehicles and areas with children and/or pets. Additionally, reed diffusers are not reusable and must be changed every time the scent is changed, or about once a month. The thin reeds or sticks that are used often become clogged up and must be thrown out.

Diffusers have recently come under environmental regulatory scrutiny due to their liquid content's levels of Volatile Organic Compound (VOC). VOCs are organic chemical compounds that have high enough vapor pressure under normal condition to significantly vaporize and enter the atmosphere. Household products such as air fresheners, insecticides, disinfectants, etc., commonly contain VOCs. VOCs are emitted as gases from certain solids and liquids and include a variety of chemicals. There are several concerns surrounding VOCs. First, VOCs combine with nitrogen oxides in the air to form ozone (commonly known as smog), which has been demonstrated to contribute to air pollution problems. Additionally, select VOCs may impact the respiratory and neurological systems causing negative health effects.

The Environmental Protection Agency, along with a number of leading equivalent state agencies in California, Maryland, Pennsylvania, New York, New Jersey, Maine, Delaware and Washington D.C. have passed stringent statutes limiting the VOC content in various consumer related products. Of these states, California has been the most stringent, specifically calling on air freshener products to limit their VOC content to 18%. Market samplings of the products currently being sold on the market revealed that over 84% of the products had VOC levels far surpassing these levels.

Many of the liquid fragrance solutions used in traditional diffusers currently sold in the marketplace contain high levels of VOCs as they act as carriers lifting molecules into the air. In order to work effectively, the VOCs must come in contact with the surrounding air, react and then lift the non-volatile ingredients into the air. Therefore, current diffusers must either have the solution exposed directly to the surrounding air (as in an open top container), or by using a device/mechanism that transfers the solution from a container to a surface that is exposed to the air (as in many closed top containers). Historically wicking mechanisms in both types of diffusers, closed and open top, did not have to be as efficient in the diffusing function owing to the fact that a high VOC content liquid being wicked/exposed had enough lift to be able to diffuse itself into the surrounding environment. When using a mechanism to transfer the solution from a container, often times, the non-volatile compounds end up clogging the 'channels' that transfer the solution through capillary action. When channels become clogged, the wick can no longer function properly and must be replaced. As VOC content is lowered, the percentage of non-volatile ingredients increase, the design and functionality of the diffuser become much more important in order to maintain diffusion efficacy. Thus, the higher the concentration of non-volatile compounds, the more likely the mechanism will clog and work less effectively.

Additionally, the surface area of exposed solution directly impacts the effectiveness of the diffuser. This is why many previous embodiments have used multiple reeds to increase the surface area of the exposed solution by creating two surfaces with which to expose the solution to the air (the reeds themselves and direct contact with the solution). The same is true for diffusers that use a mechanism to transfer the solution to an exposed surface. However, VOCs also play an important role in determining the necessary surface area. The lower the VOC content of the solution being diffused, the greater the need for a large surface area and efficient absorption in order to maintain optimal product function.

Due to the recent environmental VOC standard changes, there has developed a need for an aerator that can implement an increased concentration of non-volatile compounds (above 80%) resulting in low VOC levels without clogging. It is also desirable to ensure the diffuser has an absorption rate sufficient to quickly expose the solution to a large surface area and that the diffuser can provide a consistent flow of the solution to the surface and properly release the solution into the atmosphere.

BRIEF DESCRIPTION

In one aspect of the present invention, a spill-proof device is disclosed that is adapted to flamelessly diffuse a low volatile liquid solution into the atmosphere. The device comprises a liquid solution having less than 20% volatile organic compounds housed in a vessel with at least one wall, wherein an opening is disposed in the wall. The device further includes a wick assembly including at least a wick of porous material capable of being disposed in the opening of the vessel for at least partial submergence in the liquid solution. The wick is further disposed for drawing up the liquid solution through capillary action. The wick assembly is reusable and adapted to removably seal the opening in the vessel.

In another aspect of the present invention, a spill-proof diffuser assembly is disclosed that is adapted to flamelessly diffuse low volatile liquids into the ambient air. The assembly comprises a vessel for housing a liquid solution having an opening with a raised neck portion, an aerator top comprising a porous material having a first shallow recess and a second deeper recess concentrically disposed therein, and a wick capable of being removably disposed in the second recess. The first recess is adapted to removably engage the neck portion, and the wick is disposed for at least partial submergence in the liquid. At least one of the diffuser top and wick seal the opening of the vessel.

In yet another aspect of the present invention, a method is disclosed for flamelessly diffusing a low volatile liquid solution into the atmosphere. The method includes filling a vessel having an opening with a liquid solution having less than 20% volatile organic compound, creating a reusable, porous wick assembly comprising at least an aerator top and a wick by removably inserting at least one wick to said diffuser top; creating a spill-proof seal between said vessel and said wick assembly; and partially submerging one or more of the wicks in the liquid solution enabling the one or more wicks to transfer the liquid solution to said diffuser top through capillary action.

BRIEF DESCRIPTION OF THE DRAWINGS

The invention will take form in certain parts and arrangements of parts, preferred embodiments of which will be described in detail in this specification and illustrated in the accompanying drawings which form a part hereof and wherein:

FIG. 18 is an aerator assembly having a tongue and groove mechanism for sealing the top and wick to the vessel;

FIG. 19 is a solid top with an adhesive coating meant to be mated with the vessel opening; and FIG. 20 is a two dimensional view of an aerator assembly wherein the diffusing mechanism is a wick with a large surface area top.

DETAILED DESCRIPTION

Figure 1:
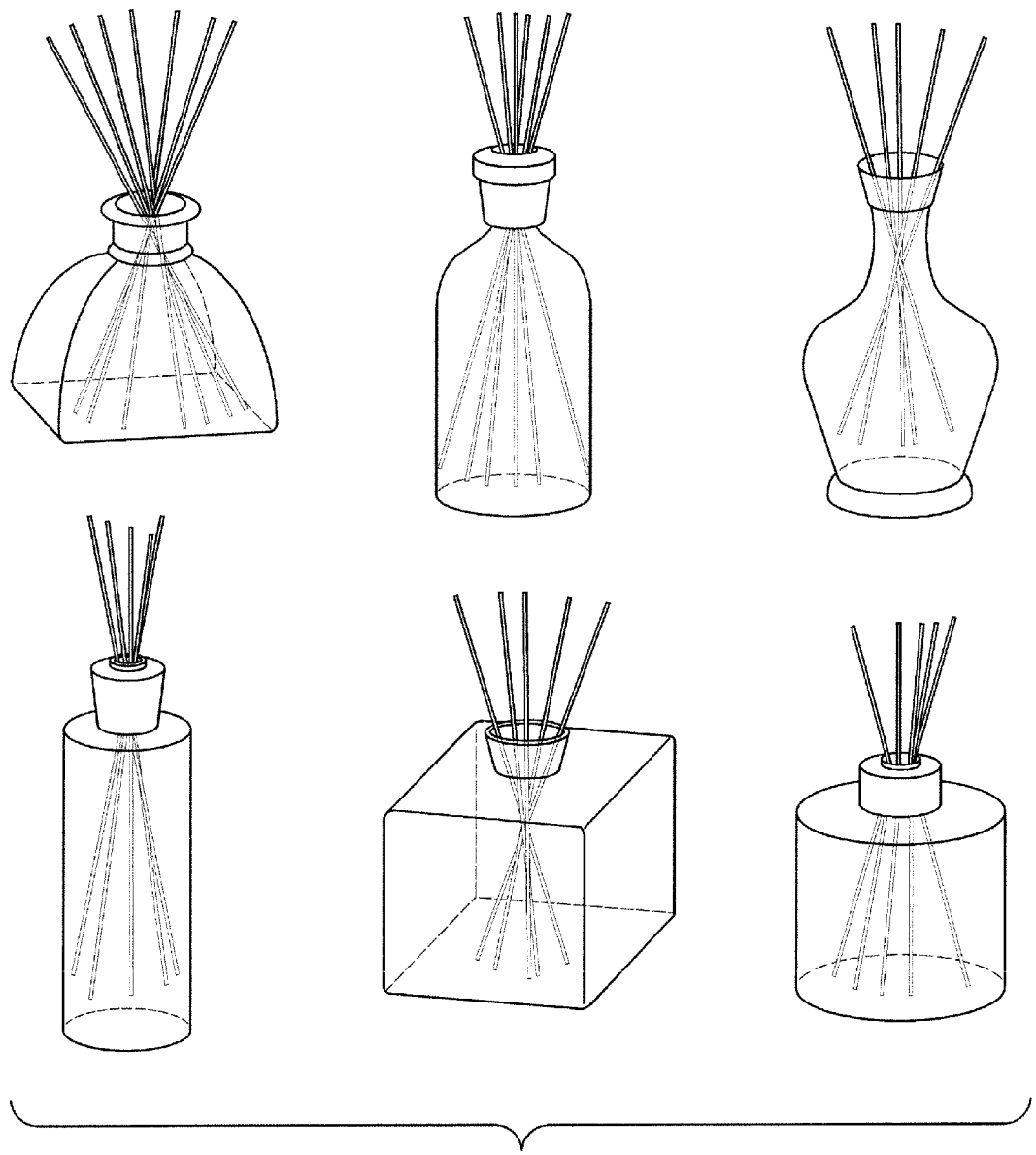
FIG. 1 is a three dimensional rendering of prior art reed diffusers.
Figure 2:
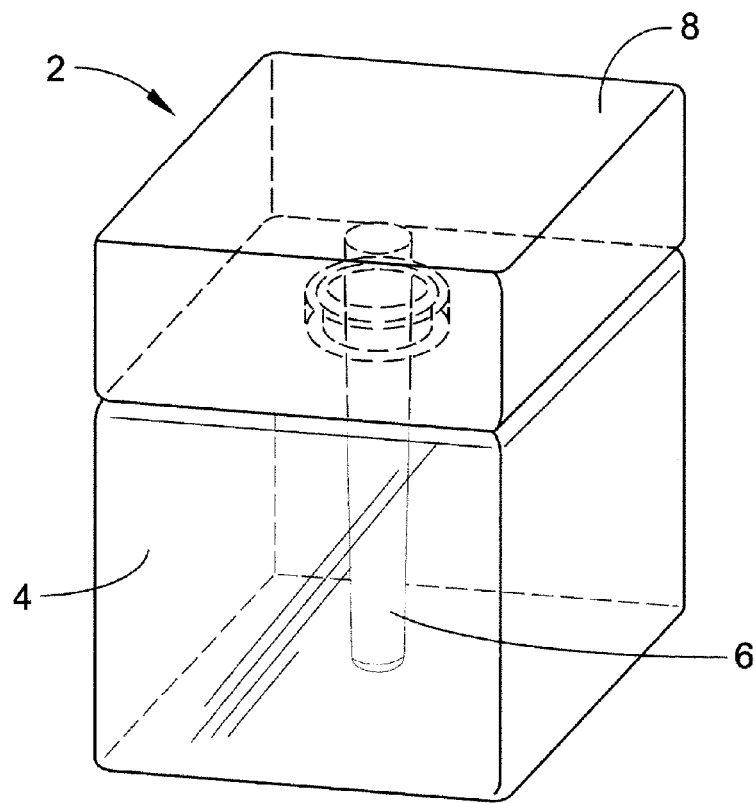
FIG. 2 is a three dimensional view of the spill-proof aerator assembly according to the present invention

Referring now to the drawings, wherein the showings are for purposes of illustrating preferred embodiments of this invention only and not for purposes of limiting the same, FIG. 2 illustrates one exemplary embodiment of the spill-proof aerator assembly 2 fully assembled, in accordance with the present invention. Aerator assembly 2 includes a two-piece wick assembly comprising solid top 8 and wick 6, inserted into the solid top 8 and partially submerged in vessel 4. Alternatively, the wick assembly could be one continuous piece. Vessel 4 is filled with a liquid solution (not shown) preferably comprising a mixture of volatile/non-volatile liquids having a volatile organic compound (VOC) level below 20%. The liquid solution may include fragrances, deodorizers, insecticides, decongestants, and the like. The exact solution composition may be optimized according to a manufacturer's specific products. However, mixing various liquids must be proportioned such that solvents with naturally higher VOCs will require the addition of a lower VOC liquid to ensure the emission is below the 20% threshold. Similarly, when the solvent has a low VOC, a higher VOC content may be implemented in the liquid.

Figure 3:
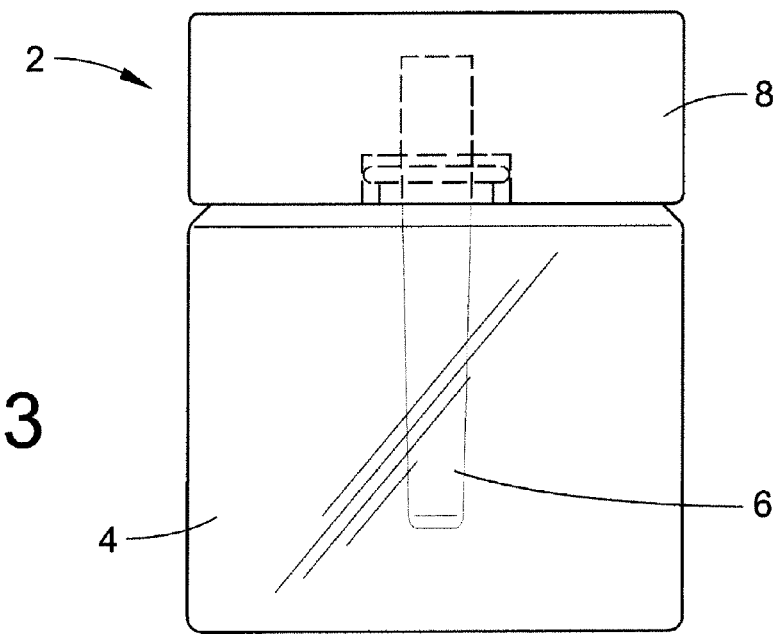
FIG. 3 is a two dimensional view of the spill-proof aerator assembly portrayed in FIG. 2 as viewed from the side.
Figure 4A:
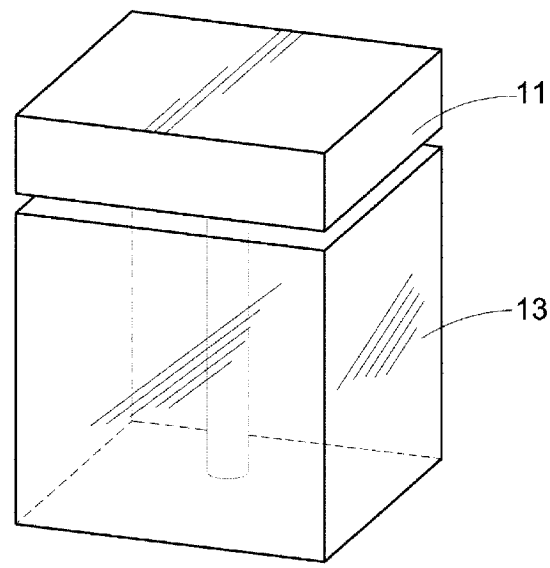
FIG. 4(a) is a three dimensional view of a spill-proof aerator assembly with a cube shaped vessel and square shaped top with a cylindrical wick.
Figure 4B:
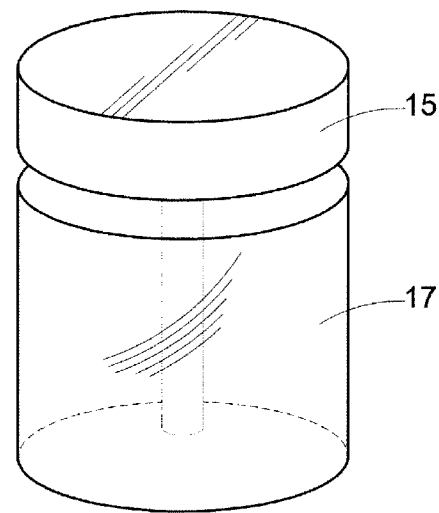
FIG. 4(b) is a three dimensional view of a spill-proof aerator assembly with a cylindrically shaped vessel, top and wick.
Figure 4C:
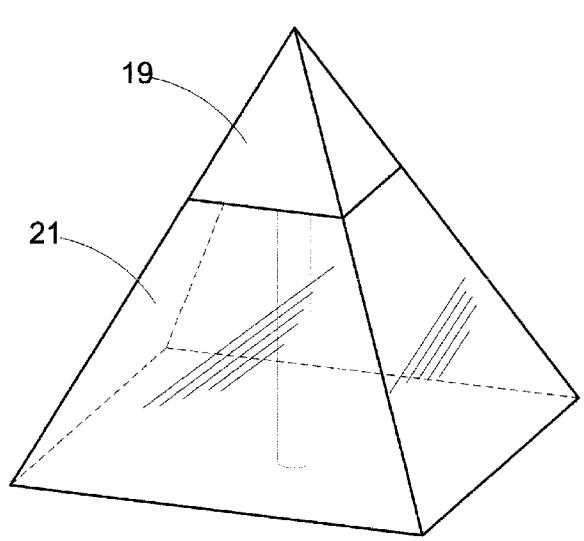
FIG. 4(c) is a three dimensional view of a spill-proof aerator assembly with a pyramid shaped vessel and top and a cylindrical wick.
Figure 4D:
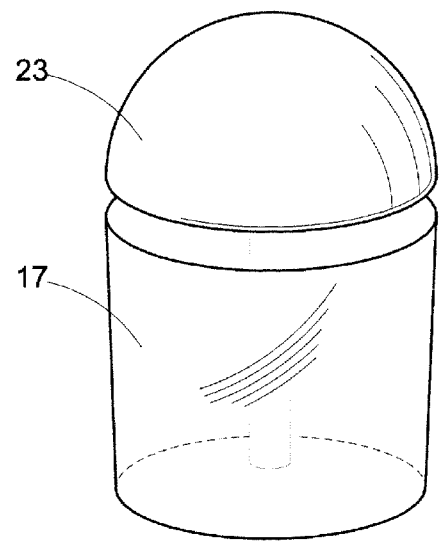
FIG. 4(d) is a three dimensional view of a spill-proof aerator assembly with a cylindrical shaped vessel with a domed top and a cylindrical wick.

FIG. 3 displays aerator assembly 2 from a side angle with solid top 8 resting snugly against vessel 4. Wick 6, extends from the solid top 8 partially through vessel 4. The aerator assembly is not limited to the particular shape or assembly displayed, and may take any form desired without affecting the function of the aerator. As illustrated in FIG. 4(a)-(d), the aerator assembly may have a cube shaped vessel 13 with a square top 11(a), a cylinder shaped vessel 17 and top 15(b), a pyramid shaped vessel 21 and top 19(c), or a cylindrical vessel 17 with a dome top 23(d). However, the aerator assembly is not limited to the exemplary shapes listed herein. It is to be appreciated that the aerator referred to herein takes on a generic shape unless otherwise specified.

Figure 5:
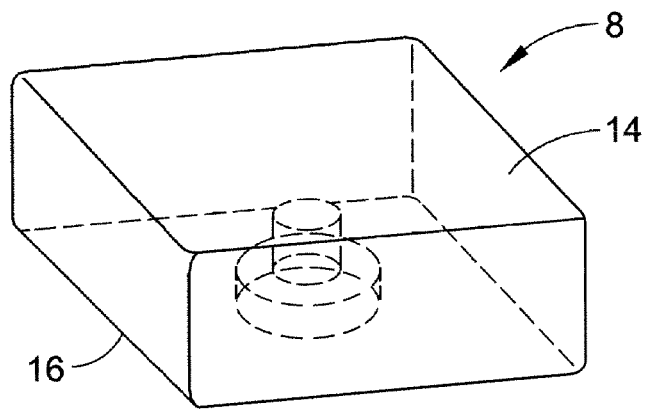
FIG. 5 is a three dimensional view of the solid top of the proposed spill-proof aerator with the wick removed.

As seen in FIG. 5, solid top 8 includes at least a top surface 14 and bottom surface 16. Solid top 8 is generally shaped so as to provide multiple evaporation faces to facilitate the release of liquid into the atmosphere; however a single face of the solid top can be used as the evaporative surface. The shape of solid top 8 is not critical, and may be, for example, a disk, square, rectangle, cone or sphere, with walls that are smooth, undulated, ribbed, grooved, flat, or formed in any other way, providing the solid top is able to evaporate the particular liquid used. Solid top 8 may be formed of a fibrous material with absorptive qualities, such as wood and ceramics, or the like.

Figure 6:
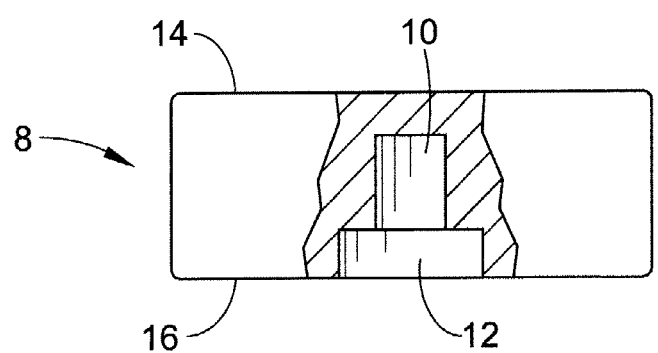
FIG. 6 is a two dimensional view of the solid top of the proposed fragrance aerator from the side with the dowel wick.

As best displayed in FIG. 6, one exemplary embodiment of solid top 8 includes a first hole 10 and a second, larger hole 12, each disposed in bottom surface 16. Neither first hole 10 nor second hole 12 fully traverse the solid top 8. Second hole 12 is larger in diameter, but shallower than first hole 10. Therefore, first hole 10 is concentrically disposed inside second hole and extends deeper into solid top 8, toward top surface 14. The solid top 8 may be formed to any thickness providing the thickness is sufficient to allow for a first hole 10 and a second hole 12, if such holes are used in the top 8. In another embodiment, solid top 2 may comprise only one hole, or no holes at all.

Figure 7:
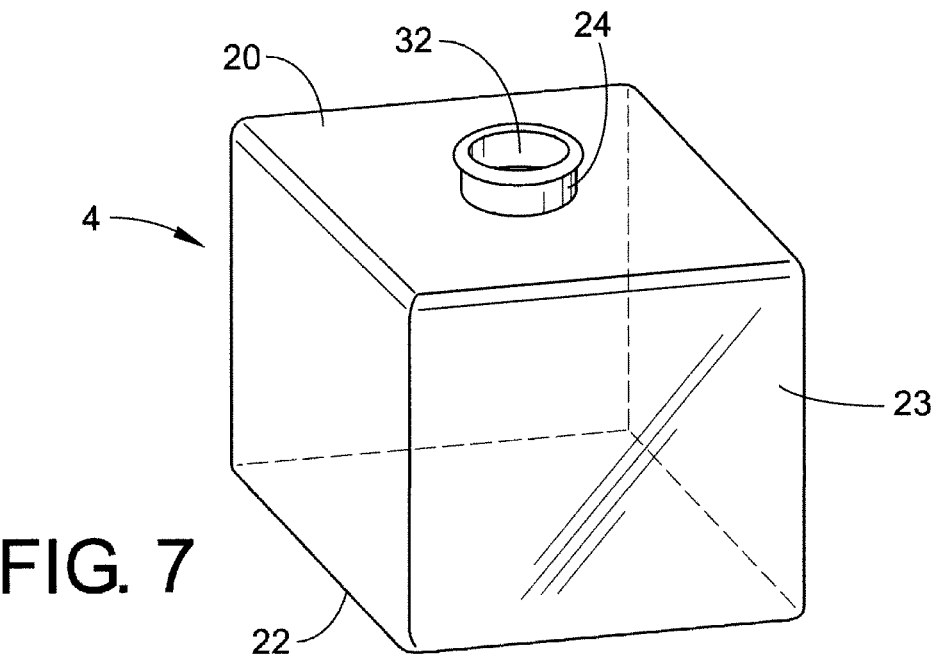
FIG. 7 is a three dimensional view of the vessel which holds the fragrance solution for diffusion having a neck portion.
Figure 8A:
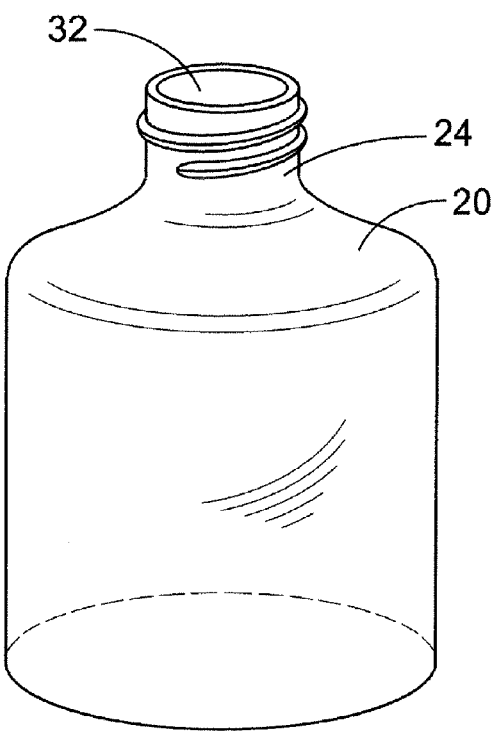
FIG. 8(a) is a cylindrical shaped vessel with a neck portion that is narrower than the rest of the vessel.
Figure 8B:
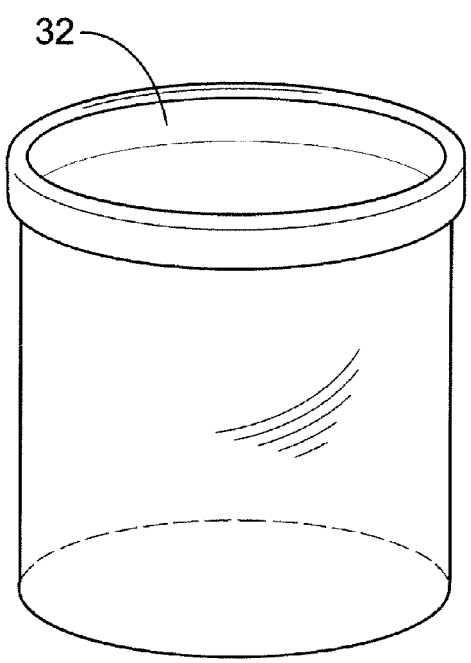
FIG. 8(b) is a cylindrical shaped vessel without a neck portion.

FIG. 7 illustrates an exemplary vessel 4 according to the present invention. Vessel 4 is depicted as being substantially cube-shaped; however, as stated previously, the particular shape and/or volume is not critical to the assembly and substantially depends on aesthetic requirements. Generally, vessel 4 includes an upper wall 20, a lower wall 22, and at least one end wall 23. Vessel 4 is preferably formed of glass. However, the vessel 4 may alternatively comprise any suitable material such as metal, porcelain, plastic, etc. According to one exemplary embodiment of the present invention, vessel 4 includes a neck portion 24, circumferentially surrounding an opening 32. Neck portion 24 is preferably more narrow than the rest of the vessel and raised above upper wall 20 to releasably engage second hole 12 of solid top 8. In this exemplary embodiment, vessel 4 includes a crimp-top neck 24 that fits snuggly inside second hole 12, creating a spill-proof seal between the solid top 8 and the vessel 4. A screw top neck on the bottle can also be utilized to the same effectiveness. When solid top engages vessel 4 creating a seal, a second spill-proof seal is created by the insertion of wick 6 through opening 32. Therefore, this particular embodiment comprises a double spill-proof seal. FIG. 8 displays two additional exemplary embodiments of the vessel opening 32. The vessel in FIG. 8(*a*) contains the narrow neck portion 24 raised above the upper wall 20. The neck portion 24 may be threaded or non-threaded for mating with the solid top 8 and wick 6 assembly. The vessel displayed in FIG. 8(*b*) does not include a neck portion and instead maintains a wide opening 32.

Wick 6 comprises a porous or fibrous material, including but not limited to wood, ceramics, fibers, plastics, or any other materials providing significant absorption. As opposed to known diffusers, the wick 6 according to the present invention may be re-used multiple times, even if the particular type of liquid is changed. Once the wick 6 completely dries and is rid of the previous liquid, it may be re-used regardless of the scent or composition of the previous liquid. Due to the particular cut, moisture level and wood material, the wick will not experience the problem of clogging known diffusers face, wherein the wicks may only be used once and then must be changed. In one embodiment, wick 6 comprises wood cut longitudinally with the wood grain in a vertical fashion. This assists in liquid uptake. If the wood was cut horizontally, capillary action will be retarded and the device will not diffuse efficiently. Moreover, it is preferable if the wood has a moisture content of less than 15% to maximize absorption and further limit clogging.

Figures 9, 10:
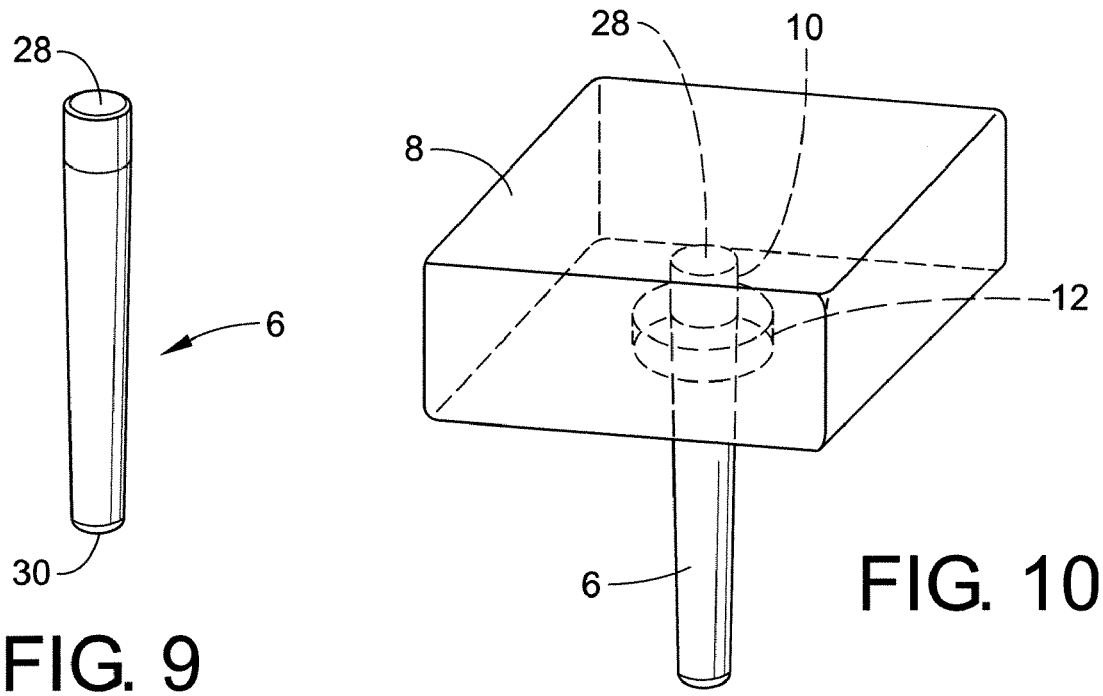
FIG. 9 is a three dimensional view of a cylindrical wick used to wick liquid into the solid top.
FIG. 10 is a three dimensional view of the solid top of the aerator assembly including the single wick which has been inserted into the solid top.
Figure 11:
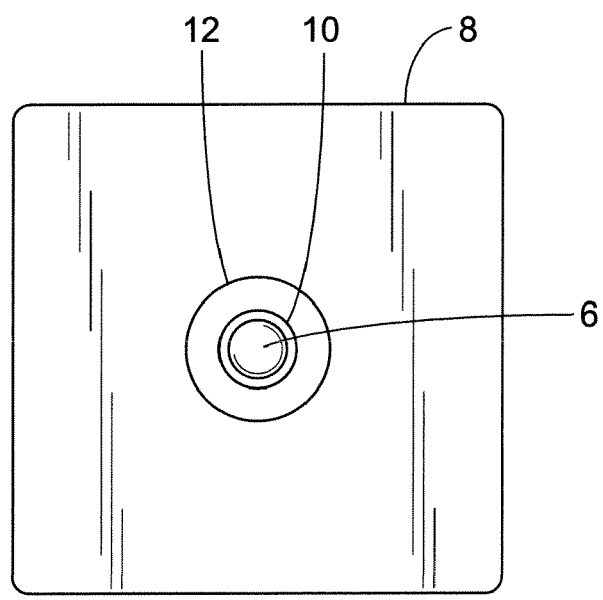
FIG. 11 is a top view of the solid top of the proposed spill-proof aerator.
Figure 12:
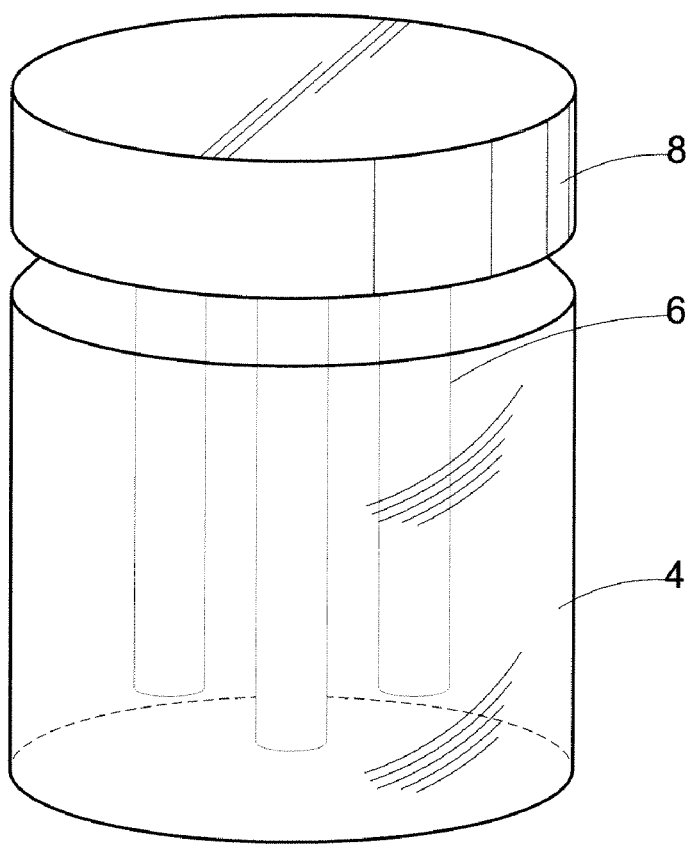
FIG. 12 is a three dimensional view of an aerator assembly employing three cylindrical wicks.
Figure 13:
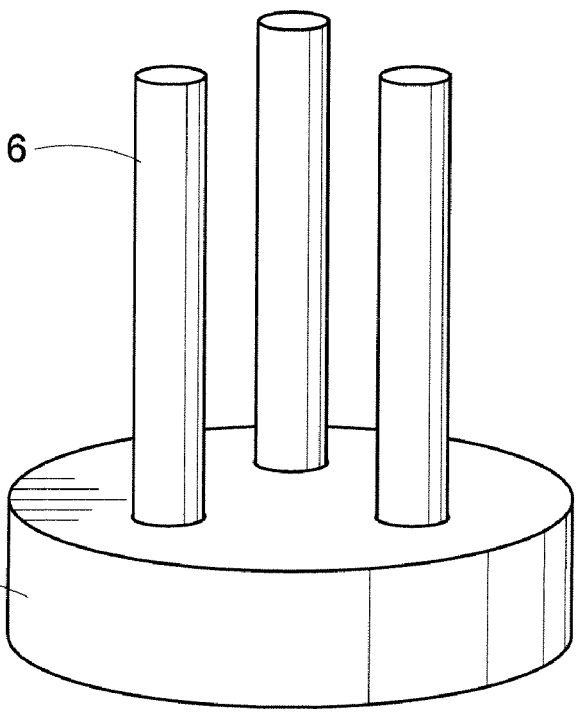
FIG. 13 is a three dimensional view of a solid top employing three cylindrical wicks turned upside down.

As shown in FIG. 9, wick 6 comprises a first end 28 extended opposite a second end 30. First end 28 is formed such that it may be releasably received by first hole 10, as best seen in FIGS. 10 and 11. Wick 6 is preferably inserted into first hole 10 by hand and the fit should be exact, thereby eliminating any need for extra tools. Wick 6 may alternatively be mated with solid top 8 in any way known in the art, such as threading, use of adhesives and interlocking connectors, so long as the liquid solution is effectively communicated from the wick 6 to solid top 8. In one embodiment, wick 6 is cylindrical in shape, with second end 30 being tapered such that first end 28 has a larger radius than second end 30. Although depicted in the figures as a cylinder, wick 6 may take on any shape appropriate for the particular aerator to be used. For example, if first hole 10 is shaped as a square, it may be necessary for first end 28 of wick 6 to be shaped as a complementary square. Additionally, an aerator may employ multiple wicks, as seen in FIGS. 12 and 13. FIGS. 12 and 13 illustrate the use of three separate wicks, each mated with first holes 10 of solid top 8. However, any number of wicks may alternatively be used.

Figure 14:
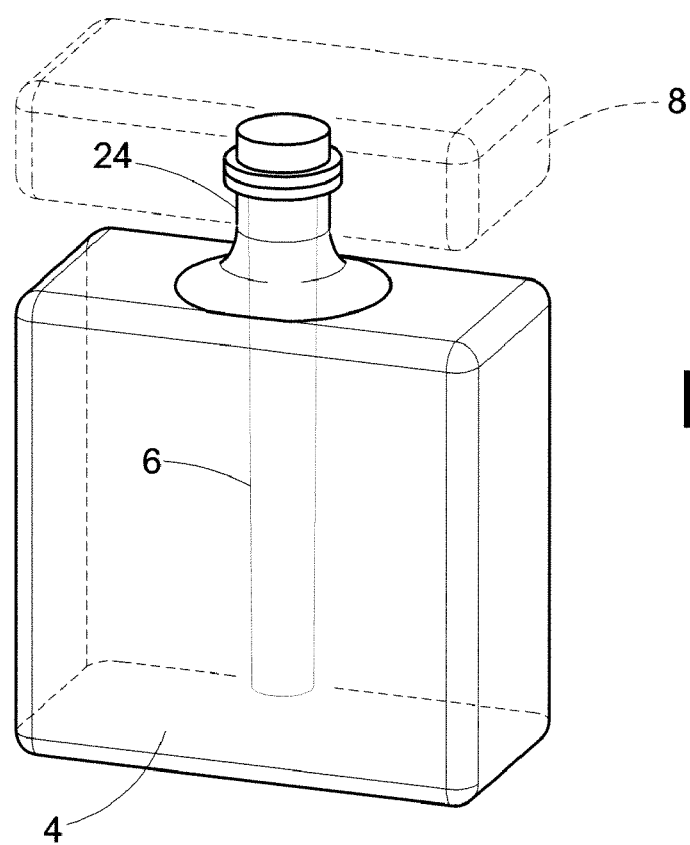
FIG. 14 is an aerator assembly using a tapered wick to seal the top of the vessel.

The spill-proof aerator of the present invention according to one exemplary embodiment, is assembled by first filling vessel 4 with a desired volatile and, optionally, nonvolatile liquid (maintaining total VOC levels below 20%). Once the liquid is disposed in vessel 4, first end 28 of wick 6 is inserted into first hole 10 of solid top 8. Second end 30 of wick 6 is then inserted through opening 32 and into vessel 4. Due to the tapered shape of wick 6, as the wick 6 is lowered into vessel 4, the width of the wick 6 increases until the wick 6 seals off the opening 32 of vessel 4, as best seen in FIG. 14. As described above, the opening 32 may alternatively, or additionally, be sealed by the engagement of solid top 8 and opening 32. Second hole 12 may be secured to neck portion 24 using a snap arrangement, screw arrangement, or any other suitable method known in the art. Solid top is preferably removable from the vessel by hand, without the use of external tools. Therefore, once assembled, solid top 8 rests flush up against vessel 4 and opening 32 is sealed off creating a spill-proof effect that will endure even if it were knocked on its side or even turned over.

Figure 15:
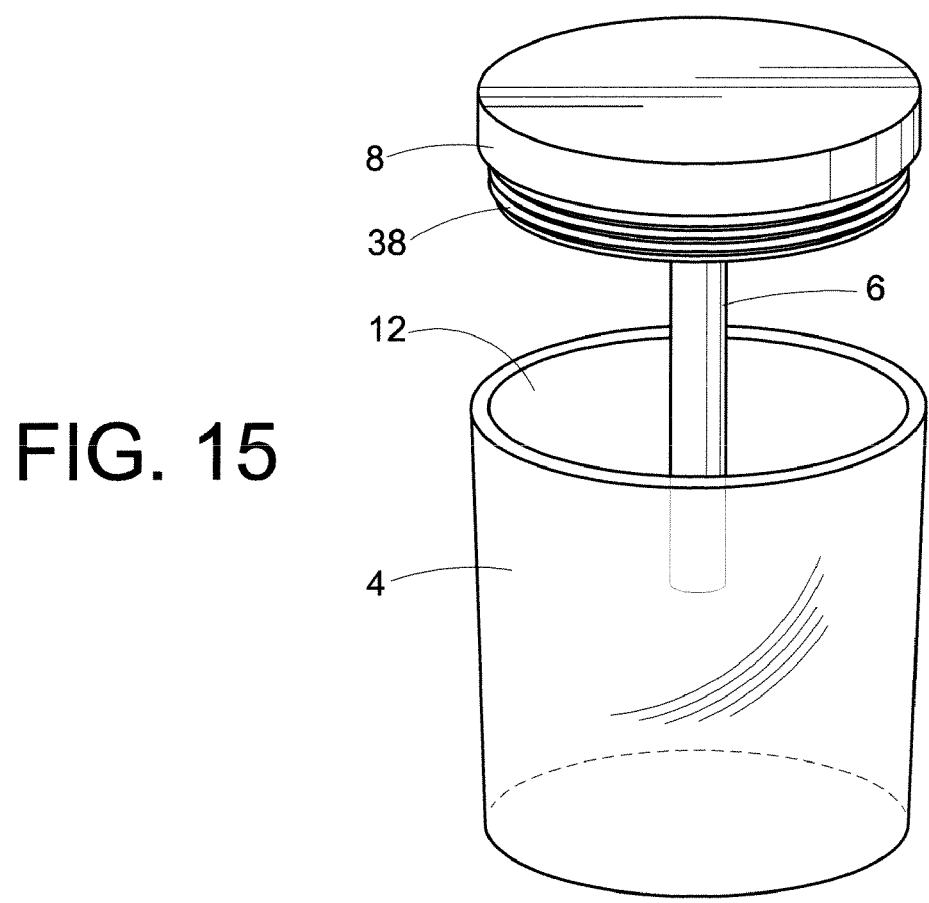
FIG. 15 is a three dimensional view of an open vessel sealed by a gasket attached to the solid top.

FIG. 15 illustrates another embodiment of the spill-proof seal of the present invention, using a gasket 38 to form a pressure seal. Gasket 38 can be either attached to solid top 8 or to vessel opening 32. Gasket 38 may be made out of any flexible material known in the art that is resistant to liquid and does not corrode or wear easily. Common gasket/seal materials that may be used include rubber, neoprene and various soft plastics. The pressure seal is created when the top/wick combo is inserted into the vessel 4 and pressed down gently.

Figure 16:
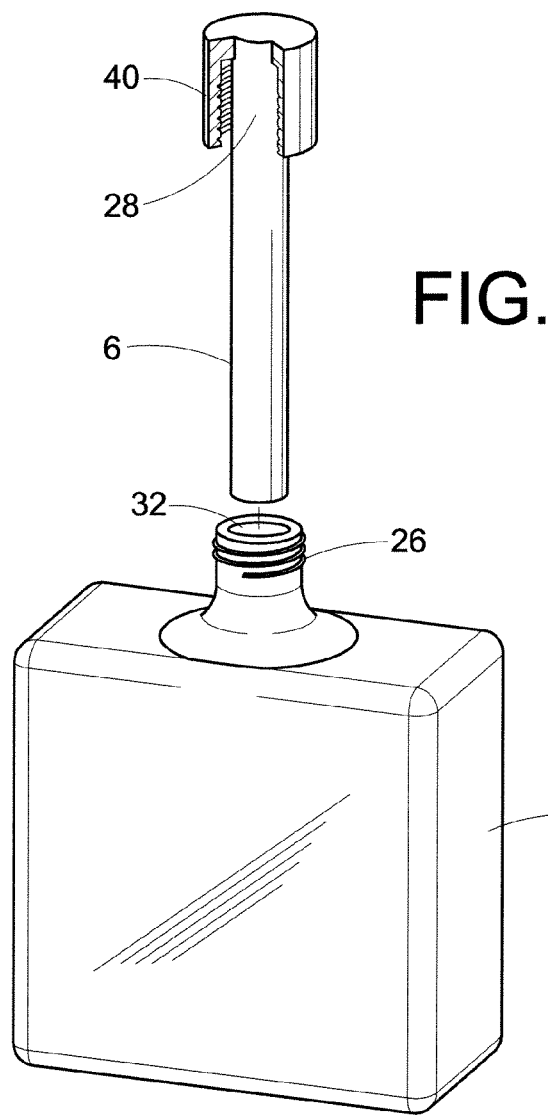
FIG. 16 is an aerator assembly having a threaded screw top wick for mating with a threaded necked vessel.

FIG. 16 displays yet another embodiment of the spill-proof seal according to the present invention. Vessel 4 includes a threaded neck 26 that is adapted to engage a threaded cap 40 that fits over first end 28 of wick 6 and creates a tight seal. FIG. 16 shows how the threaded cap 40/wick 6 arrangement is then securely mated with an opening 32.

Figure 17:
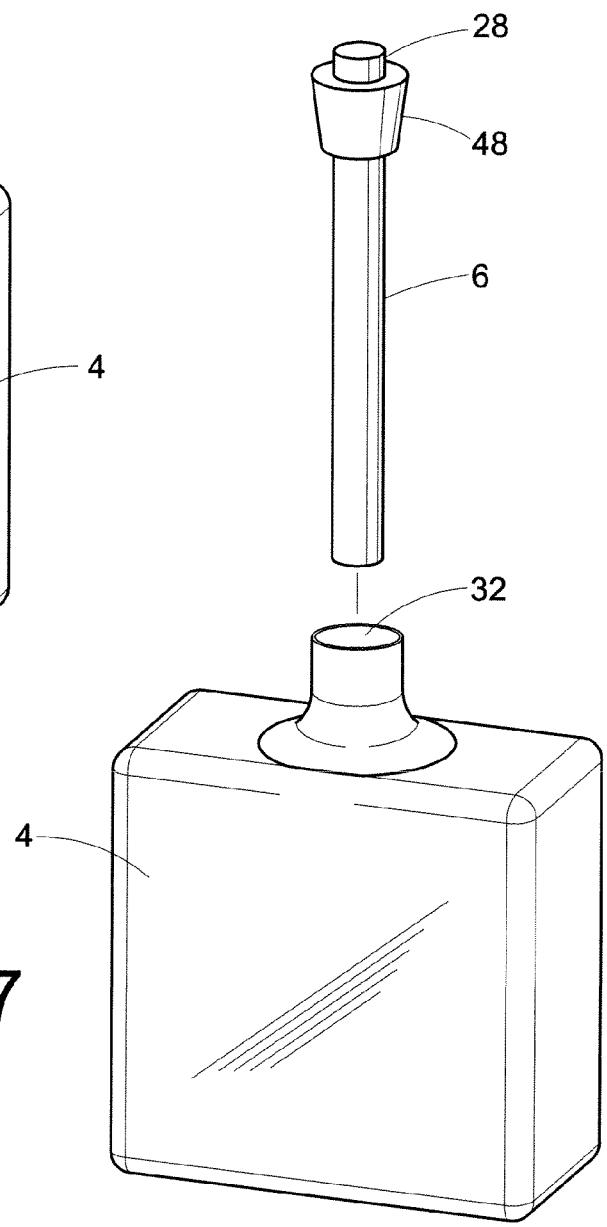
FIG. 17 is an aerator assembly having a stopper based mechanism attached to the wick for insertion into the vessel opening and creating a seal.

In another embodiment of the present invention seen in FIG. 17, a stopper/gasket 48 is attached to wick 6, close to first end 28. Wick 6 is then inserted into opening 32 of vessel 4 to create a spill-proof seal. The stoppered wick 6 can then be mated to solid top 8 through the various methods described above. Similar to the gasket seal, the stopper 48 can be made of a number of flexible materials that are impervious to liquids including, but not limited to rubbers, plastics, neoprene, and similar materials.

In yet another embodiment of the present invention, as seen in FIG. 18, a spill-proof seal is created by employing a tongue and groove mechanism between the solid top 8, wick 6 and the vessel 4. Vessel 4 has a tongue 50 protruding inwards on opening 32, similar to an inner tube. Tongue 50 can be made from a number of flexible, liquid impervious material such as rubber or various plastics. Solid top 8 has a separate grooved piece 52, which is made to fit the tongue 50 and fits snuggly when the top/wick combo is pressed unto vessel 4. Additionally, FIG. 19 displays another exemplary embodiment for creating a spill-proof seal between the vessel 4 and solid top 8. An adhesive may be applied to hole 53 of solid top 8, which is then mated on to vessel neck 24. The adhesive may be a commercially available adhesive. This method of adhesion may also be used on no-neck vessels.

The spill-proof aerator assembly may alternatively not include a solid top, and diffusion into the atmosphere occurs completely through the wick 6, as displayed in FIG. 20. The wick 6 preferably expands as it extends out of the vessel opening 32 creating a larger surface area to optimize diffusion.

The spill-proof aerator for low volatile organic compound liquids, once assembled and filled with the liquid solution, uses the natural properties of the solid top 8 and the wick 6 to diffuse the liquid into the air. The one or more wicks 6 act as a sponge and soak up the liquid contained in the vessel through capillary action. The liquid then travels through the wick 6 and into the solid top 8, whereby through further capillary action, the solid top becomes soaked in the liquid. This wicking action through the wick and the top begins the diffusion process through the air as the liquid reaches the surface of the top.

Since solid top 8 is solid and the vessel 4 is sealed, through either a single or double seal, there is no need for maintenance of the spill-proof aerator. After initial assembly and insertion, no further user action is required. The solid top will continue to diffuse and the wick will continue to "wick" until all of the liquid solution in the vessel has been used. Once all the liquid has been used, the solid top 8/wick 6 assembly may be removed from engagement with vessel 4 and vessel 4 may be refilled with liquid to be diffused.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

What is claimed is:

1. A spill-proof device adapted to flamelessly diffuse a liquid solution into the atmosphere, said device comprising:
- liquid solution having less than 20% volatile organic compounds;
- a vessel for housing said liquid solution, said vessel having at least one wall, with an opening disposed in said wall;
- a reusable wick assembly comprising a wick of porous material and an aerator top, said wick being tapered and having a wide end and a narrow end, said narrow end capable of being disposed in said opening in said vessel for at least partial submergence in said liquid solution and of drawing up said liquid solution thorough capillary action, and wherein said wide end is wider than said opening and is adapted to removably seal said opening.

2. A device according to claim 1, wherein said wick assembly comprises said wick being disposed in said aerator top.

3. A device according to claim 1, wherein said top further comprises a first shallow recess and a second deeper recess concentrically disposed therein.

4. A device according to claim 3, wherein said first recess is adapted to mate with said vessel by removably engaging a raised neck portion surrounding said opening.

5. A device according to claim 3, wherein said second recess is adapted to removably engage said wick.

6. A device according to claim 1, wherein said wick assembly comprises absorptive materials.

7. A device according to claim 1, wherein said vessel is capable of being refilled with the liquid solution by removing the wick assembly from engagement with said vessel and filling said vessel with additional liquid solution.

8. A device according to claim 1, wherein said porous material is wood.

9. A device according to claim 8, wherein said wood material of said wick assembly is cut longitudinally along the wood grain.

10. A device according to claim 8, wherein said wood material has a moisture content of less than 15%.

11. A device according to claim 1, wherein said vessel includes a raised neck portion surrounding said opening, wherein said neck portion is adapted to releasably engage said wick assembly.

12. A device according to claim 11, wherein said neck portion is threaded and adapted to engage a complementary threaded portion of said wick assembly.

13. A device according to claim 1, wherein said liquid solution comprises at least one of a fragrance, a medicine, and an insecticide comprising at least one of volatile and non-volatile compounds.

14. A device according to claim 1, wherein said aerator top and said wide end of said wick form a double seal with said vessel opening.

15. A spill-proof aerator assembly adapted to flamelessly diffuse non-volatile liquids into the ambient air, comprising:
- a vessel for housing a liquid solution having an opening with a raised neck portion;
- an aerator top comprising a porous wood material having a first shallow recess and a second deeper recess concentrically disposed therein; and
- a tapered wick, having a narrow end capable of being removably disposed in said second recess, wherein said first recess is adapted to removably engage said neck portion, and a wide end, having a greater width than said opening, capable of being disposed for at least partial submergence in said liquid, wherein at least said wide end is adapted to said seal the opening of said vessel, wherein said non-volatile liquid has less than 20% volatile organic compounds.

16. A spill-proof aerator assembly according to claim 15, wherein said aerator top and said wide end of said wick form a double seal with said vessel opening.

17. A method for flamelessly diffusing a liquid solution into the atmosphere, comprising:
- filling a vessel having an opening with a liquid solution having less than 20% volatile organic compound;
- creating a wick assembly comprising at least an aerator top and at least
- one wick, by removably inserting at least one wick into said aerator top,
- said wick assembly comprising a reusable porous material;
- creating a spill-proof seal between at least said vessel and said at least one wick by tapering said wick, such that one end is wider than said opening and the other end is more narrow, and inserting said narrow end into said opening until said wick becomes too wide; and
- partially submerging said at least one wick in the liquid solution enabling the at least one wick to transfer the liquid solution to said aerator top through capillary action.

18. The method according to claim 17, said method further comprising refilling said vessel when empty with the liquid solution by removing said top and wick from engagement with said vessel and filling the vessel with additional liquid solution.

19. The method according to claim 17, further including providing a first shallow recess in said aerator top and a second deeper recess concentrically disposed therein.

20. The method according to claim 19, further including adapting said second recess to releasably engage said wick.

21. The method according to claim 19, further including adapting said first recess to mate with said vessel by removably engaging the opening of said vessel.

22. The method according to claim 17, wherein said liquid solution is at least one of a fragrance, a medicine, and an insecticide.

\* \* \* \* \*